Feb. 14, 1961 P. J. JENKINS Plant Pat. 2,024
APPLE TREE
Filed May 2, 1960
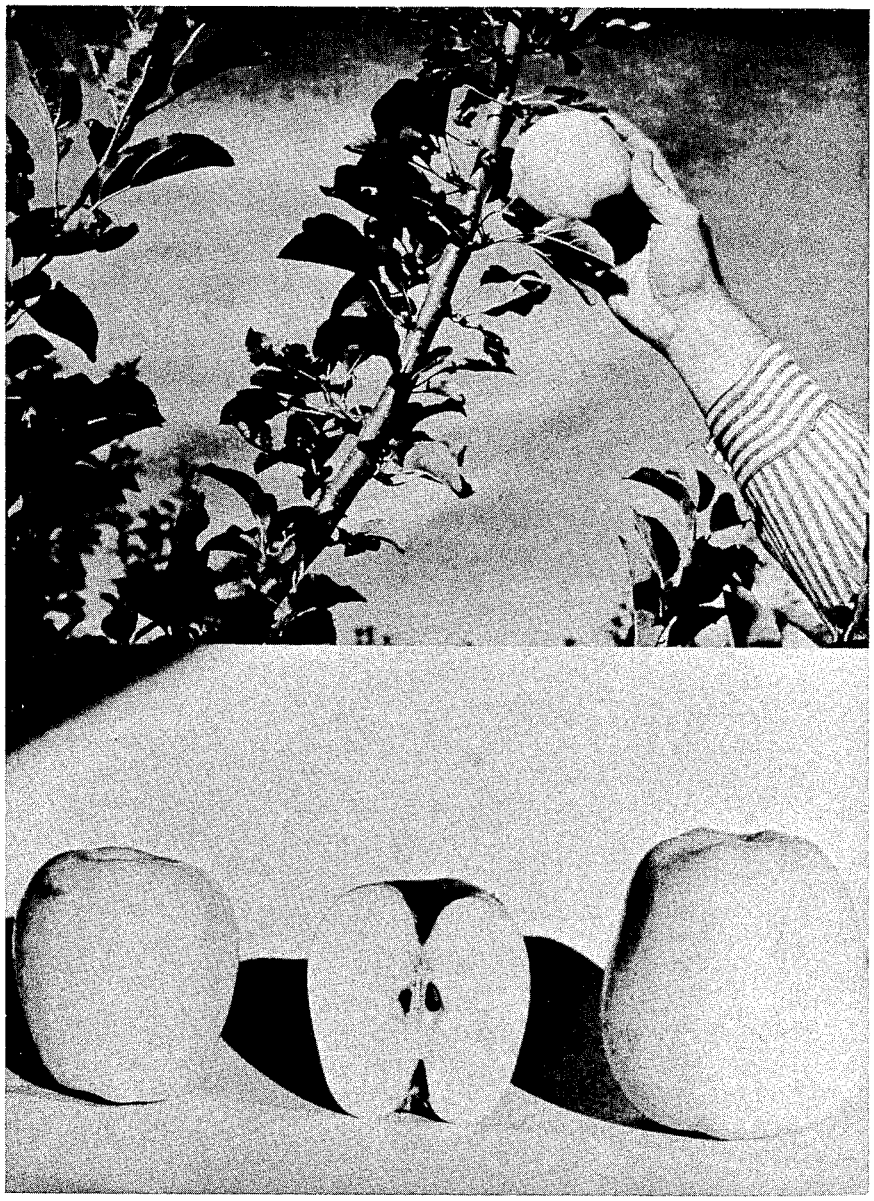
INVENTOR
Philip J. Jenkins
BY Robb & Robb
ATTORNEYS United States Patent Office Plant Pat. 2,024
Patented Feb. 14, 1961

2,024

APPLE TREE

Philip J. Jenkins, Parker, Wash., assignor, by mesne assignments, to Stark Bro's Nurseries and Orchards Company, Louisiana, Mo., a corporation of Missouri Filed May 2, 1960, Ser. No. 26,388

1 Claim. (Cl. 47—62)

The present invention relates to a new and distinct variety of apple tree which was discovered by me as a whole tree sport during the course of management of an orchard near Parker, Yakima County, Washington, owned by my employer, who is the assignee of this application.

At the time of my initial discovery of the new variety aforesaid, I was engaged in making a routine orchard inspection on the property referred to above, and during the course thereof, my attention was attracted to a tree amongst those of the variety "Golden Delicious" (unpatented) which appeared to be different in its habit of growth, as more particularly evidenced by the fact that contrary to the regular "Golden Delicious" variety, it was characterized by a spur-type habit of bearing fruit relatively close together along the laterals. Closer inspection and subsequent continuous observations and tests showed that this spur type characteristic of the new variety was fixed and established and, in addition, I further found that the tree possessed a semi-dwarf habit and attains a size approximately two-thirds that of the standard "Golden Delicious."

Additional outstanding and distinctive characteristics were also observed, which altogether represent a unique combination in an apple tree, said combination being briefly summarized as follows:

(1) A semi-dwarf habit of growth;

(2) Production of many more fruiting spurs than the variety "Golden Delicious" at an early age;

(3) Compact spurry growth comparable to that of the Bisbee Apple (Plant Patent No. 1,565) with the spurs, flower buds and shoots being much thicker in caliper than those of "Golden Delicious" and the spurs being borne much closer together on the laterals;

(4) A fruit form which is broader at the base and longer than the fruit of "Golden Delicious," with 5 large, relatively conspicuous points at the calyx end; and (5) High productivity of fruit that is comparable in quality to the fruit of "Golden Delicious."

The foregoing characteristics definitely differentiate my new variety from the variety "Golden Delicious," as well as from all other varieties of which I am aware. The new variety has been asexually reproduced by me by budding, as performed at Parker, Yakima County, Washington, as well as on my behalf at Louisiana, Pike County, Missouri.

The accompanying drawing shows a typical specimen branch of a tree of my new apple variety and which is illustrative of its spur-type fruiting habit, as well as typical specimens of the fruit, one of said fruit specimens being depicted in cross section.

The following is a detailed description of the new variety, with color terminology in accordance with Ridgway's Color Standards and Nomenclature (hereafter abbreviated as "Ridgway"), Horticultural Colour Chart (hereinafter abbreviated as "HCC"), Munsell Color Chart (hereinafter abbreviated as "Munsell"), as indicated, except where general color terms of ordinary dictionary significance are obvious, as based upon observations made from specimens grown at Parker, Yakima County, Washington:

Tree: Medium small; semi-dwarf; vigorous; upright; open; hardy; productive; regular bearer.

*Trunk.*—Stocky; smooth.

*Branches.*—Thick; smooth. Color—Light Grayish Olive, Plate XLVI, color No. 21'''', tone *b*, "Ridgway." Lenticels—numerous; large.

*Leaves.*—Medium large; medium thickness; rugose. Length—about 4 inches. Width—about 2¼ inches. Shape—oval (abruptly pointed). Color—Parsley Green, Plate 00962/2, page 193, vol. II, "HCC." Margin—coarsely serrate. Petiole—medium short (about ⅞ inch); medium thickness.

Flowers: Medium late (first bloom about April 15 and full bloom about April 25); medium large. Color—white, with pink tinge.

Fruit:

*Maturity when described.*—Eating ripe.

*Size.*—Variable. Axial diameter—from 3½ inches to 4 inches. Transverse diameter—from 3 inches to about 4 inches.

*Form.*—Truncate at base; conical; ribbed.

*Cavity.*—Symmetrical; rounded at base; apex acute; undulate. Depth—¾ inch. Breadth—1⅛ inches.

*Basin.*—Symmetrical; abrupt at base; wide base; undulate; crowned; glabrous. Depth—⅜ inch. Breadth—1⅛ inches. Markings—none.

*Stem.*—Medium slender; pubescent. Length—¾ inch. Breadth—⅛ inch.

*Calyx.*—Open; segments persistent; acute; separated; reflexed from base at apex. Length—3/16 inch. Outer surface—pubescent. Inner surface—pubescent.

*Eye.*—Large; open.

*Skin.*—Thin; tough; smooth; oily. Dots—conspicuous, many, small, raised, ruptured, circular; color—Sayal Brown, Plate XXIX, color No. 15'', "Ridgway"; distribution—distributed over entire surface, but mostly near basin. Ground color—Dresden Yellow, Plate 64/2, page 64, vol. I, "HCC." Color markings—from Strong Pink, Plate 2.5R 7/8, "Munsell," to Deep Pink, Plate 2.5R 6/11, "Munsell," occasionally blushed.

*Bloom.*—Wanting.

*General color effect.*—Yellow.

*Flesh.*—Juicy. Color—white with yellow tint. Texture—firm; fine. Flavor—subacid; mild; rich. Aroma—distinct. Quality—best.

*Core.*—Median. Bundle area—medium small; cordate; symmetrical; acute at base. Halves of core—equal. Bundles—inconspicuous, in two whorls; color—green tinged. Core lines—meeting. Carpellary area—distinct; small. Calyx tube—glabrous toward base, cone-shaped; entire depth—½ inch. Styles—present; united toward base. Stamens—in one median whorl. Axillary cavity—wanting. Seed cells—closed, axile; cell walls—thick, tough, length—⅝ inch, breadth—⅜ inch; longitudinal section—broadly ovate, obtuse at apex; surface—fissured; cross section—broad.

Seeds:

*Number.*—10 perfect; none imperfect; 2 per cell. Length—⅜ inch. Breadth—3/16 inch.

*Form.*—Acute.

*Color.*—Mars Brown, Plate XV, color No. 13', "Ridgway."

Use: Market; dessert; culinary.

Keeping quality: Good; from about 90 to 120 days in ordinary storage.

I claim:

A new and distinct variety of apple tree, substantially as herein shown and described, characterized particularly as to novelty by the unique combination of a semi-dwarf habit of growth, production of many fruiting spurs at an early age, a compact spurry growth comparable to that of the Bisbee Apple variety (Plant Patent No. 1,565), with the spurs, flower buds and shoots of much thicker caliper than those of the variety "Golden Delicious" and the spurs being borne much closer together on the laterals, a fruit form which is broader at the base and longer than the fruit of "Golden Delicious," said fruit having five large, relatively conspicuous points at the calyx end, and a high productivity of fruit comparable in quality to the fruit of "Golden Delicious."

No references cited.